US007280215B2

(12) United States Patent
Salnik et al.

(10) Patent No.: US 7,280,215 B2
(45) Date of Patent: Oct. 9, 2007

(54) PHOTOTHERMAL SYSTEM WITH SPECTROSCOPIC PUMP AND PROBE

(75) Inventors: Alex Salnik, Castro Valley, CA (US); Jon Opsal, Livermore, CA (US); Lena Nicolaides, Castro Valley, CA (US)

(73) Assignee: Therma-Wave, Inc., Fremont, CA (US)

( * ) Notice: Subject to any disclaimer, the term of this patent is extended or adjusted under 35 U.S.C. 154(b) by 198 days.

(21) Appl. No.: 10/947,925

(22) Filed: Sep. 23, 2004

(65) Prior Publication Data

US 2005/0062971 A1    Mar. 24, 2005

Related U.S. Application Data

(60) Provisional application No. 60/505,458, filed on Sep. 24, 2003.

(51) Int. Cl.
*G01N 21/55* (2006.01)
(52) U.S. Cl. ........................................ 356/432; 356/445
(58) Field of Classification Search ................ 356/432, 356/445
See application file for complete search history.

(56) References Cited

U.S. PATENT DOCUMENTS

| | | | |
|---|---|---|---|
| 4,634,290 A | 1/1987 | Rosencwaig et al. ........... 374/5 |
| 4,636,088 A | 1/1987 | Rosencwaig et al. ........... 374/5 |
| 4,646,088 A | 2/1987 | Inoue .................... 340/870.31 |
| 4,854,710 A | 8/1989 | Opsal et al. ................. 356/432 |
| 4,999,014 A | 3/1991 | Gold et al. .................. 356/632 |
| 5,042,951 A | 8/1991 | Gold et al. .................. 356/369 |
| 5,074,669 A | 12/1991 | Opsal ........................ 356/445 |
| 5,206,710 A | 4/1993 | Geiler et al. ................. 356/432 |
| 5,270,797 A * | 12/1993 | Pollak et al. ................ 356/432 |
| 5,293,215 A | 3/1994 | Pfendler et al. ............. 356/477 |
| 5,365,334 A * | 11/1994 | Bottka ........................ 356/432 |
| 5,408,327 A | 4/1995 | Geiler et al. ................. 356/432 |
| 5,608,526 A | 3/1997 | Piwonka-Corle et al. ... 356/369 |
| 5,706,094 A * | 1/1998 | Maris ......................... 356/432 |
| 5,741,070 A | 4/1998 | Moslehi ...................... 374/161 |
| 5,864,393 A * | 1/1999 | Maris ......................... 73/800 |

(Continued)

OTHER PUBLICATIONS

S. Holé et al., POSTER entitled "Wavelength Multiplexed Photoreflectance for submicronic thermal imaging," *12 ICPPP*, Toronto, Jun. 24-27, 2002, 1 page in length.

(Continued)

*Primary Examiner*—Richard A. Rosenberger
(74) *Attorney, Agent, or Firm*—Stallman & Pollock LLP

(57) ABSTRACT

The ability of a Modulated Optical Reflectivity (MOR) or Thermal Wave (TW) system to measure characteristics of a sample based on the amplitude and phase of a probe beam reflected from the surface of the sample can be improved by providing a polychromatic pump and/or probe beam that can be scanned over a wide spectral range, such as a range of at least 100 nm. The information contained in the spectral dependencies of a TW response obtained from the sample can be compared and/or fitted to corresponding theoretical dependencies in order to obtain more precise and reliable information about the properties of the particular sample than is available for single-wavelength systems. This information can further be combined with measurements taken for varying spot separations or varying pump source modulation frequency, as well as with photo-thermal radiometry (PTR), spectroscopic reflectometry, and/or ellipsometry measurements.

60 Claims, 11 Drawing Sheets

U.S. PATENT DOCUMENTS

| | | | |
|---|---|---|---|
| 5,900,939 A | 5/1999 | Aspnes et al. | 356/369 |
| 5,978,074 A | 11/1999 | Opsal et al. | 356/72 |
| 5,982,499 A * | 11/1999 | Chichester et al. | 356/432 |
| 6,049,220 A | 4/2000 | Borden et al. | 324/765 |
| 6,081,127 A | 6/2000 | Wagner et al. | 324/765 |
| 6,323,951 B1 | 11/2001 | Borden et al. | 356/502 |
| 6,532,070 B1 | 3/2003 | Hovinen et al. | 356/369 |
| 2003/0150993 A1 | 8/2003 | Nicolaides et al. | 250/339.11 |
| 2003/0234932 A1 | 12/2003 | Nicolaides et al. | 356/445 |
| 2004/0104352 A1 | 6/2004 | Opsal et al. | 250/372 |
| 2004/0253751 A1 | 12/2004 | Salnik et al. | 438/16 |

OTHER PUBLICATIONS

S. Holé et al., "Wavelength multiplexed photoreflectance for submicronic thermal imaging," *12 ICPPP*, Toronto, Jun. 24-27, 2002 (*Book of Abstracts*), p. 125.

G. Tessier et al., "Quantitative thermal imaging by synchronous thermoreflectance with optimized illumination wavelengths," *Applied Physics Letters*, vol. 78, No. 16, Apr. 16, 2001, pp. 2267-2269.

S. Holé et al., "Submicronic thermal imaging by wavelength multiplexed photoreflectance technique," *Electronic Letters*, vol. 38, No. 17, Aug. 15, 2002, pp. 986-987.

J.A. Batista et al., "Contrast and sensitivity enhancement in Photothermal Reflectance Microscopy through the use of specific probing wavelengths: applications to microelectronics," *Analytical Sciences*, vol. 17 Special Issue, Apr. 2001, pp. S73-S75.

G. Tessier et al., "Measuring and predicting the thermoreflectance sensitivity as a function of wavelength on encapsulated materials," *Review of Scientific Instruments*, vol. 74, No. 1, Jan. 2003, pp. 495-499.

* cited by examiner

PHOTOTHERMAL SYSTEM WITH SPECTROSCOPIC PUMP AND PROBE

CLAIM OF PRIORITY

This application claims priority to U.S. Provisional Patent No. 60/505,458, entitled "Photothermal System with Spectroscopic Pump and Probe," filed Sep. 24, 2003, which is hereby incorporated herein by reference.

TECHNICAL FIELD OF THE INVENTION

The present invention relates to optical methods for inspecting and analyzing semiconductor wafers and other samples.

BACKGROUND

There is a great need in industries such as the semiconductor industry for sensitive metrology equipment that can provide high resolution and non-contact evaluation capabilities, such as for product silicon wafers as those wafers pass through the implantation and annealing fabrication stages. In recent years a number of products have been developed for the nondestructive evaluation of semiconductor materials. One such product has been successfully marketed by the assignee herein under the trademark Therma-Probe (TP). This system incorporates technology described in the following U.S. Pat. Nos. 4,634,290; 4,636,088; 4,854,710; 5,074,669; and 5,978,074. These patents are each hereby incorporated herein by reference.

In one basic device described in these patents, an intensity modulated pump laser is focused on a sample surface for periodically exciting the sample. In the case of a semiconductor, thermal and carrier plasma waves are generated close to the sample surface that spread out from the pump beam spot inside the sample. These waves reflect and scatter off various features and interact with various regions within the sample in a way that alters the flow of heat and/or carrier plasma from the pump beam spot.

The presence of the thermal and carrier plasma waves affects the reflectivity R at the surface of the sample. Features and regions below the sample surface, such as an implanted region or ultra-shallow junction, can alter the propagation of the thermal and carrier plasma waves, thereby changing the optical reflective pattern at the surface. By monitoring the changes in R of the sample at the surface, information about characteristics below the surface can be obtained.

In the basic device, a second laser having a wavelength different from that of the pump laser is provided for generating a probe beam of radiation. This probe beam is focused collinearly with the pump beam and reflects off the sample surface. A photodetector is provided for monitoring the power of reflected probe beam. This photodetector generates an output signal which is proportional to the reflected power of the probe beam and is therefore indicative of the varying reflectivity. A lock-in detector is used to measure both the in-phase (I) and quadrature (Q) components of the signal. The two channels of the output signal, namely the amplitude ($A^2=I^2+Q^2$) and phase ($\Theta=\tan^{-1}(I/Q)$) channels, are conventionally referred to as the Modulated Optical Reflectivity (MOR) or Thermal Wave (TW) signal amplitude and phase, respectively.

In the MOR system described in these patents, pump and probe beams are used that each operate at a single wavelength. Characterization of a semiconductor sample is therefore based on a single-point correlation of experimentally obtained TW parameters (amplitude and/or phase) with the properties of interest. Due to the variety of thermal, optical, and electronic characteristics of a semiconductor that may change during the technological process, the ability of this single-point correlation to provide accurate information about sample properties is limited. This limited ability prevents a theoretical model from being applied to accurately and quantitatively describe various physical processes behind the TW signal.

Additional efforts to increase the measurement capabilities of these MOR systems included varying the distance between the pump and probe beam spots; varying the modulation frequency of the pump source; and combining the TW data with other measured data such as from photothermal radiometry (PTR), spectroscopic reflectometry, and/or ellipsometry. Such efforts are described, for example, in U.S. Patent Application Publication No. 2003/0150993, filed Dec. 10, 2002, and Application Publication No. 2003/0234932, filed May 16, 2003, as well as U.S. Pat. No. 6,532,070, each of which is hereby incorporated herein by reference. Many such "combined" systems, however, require separate measurement systems. Further, many existing systems are based on single-wavelength TW data, such that varying the modulation frequency and/or pump-probe beam offset in most cases results in featureless TW signal dependencies that are hard to use for quantitative analysis and comparison (fitting) to the theoretical model.

Other attempts to improve MOR system performance have each included an application-specific selection (or selections) of the optimal probe beam wavelength in order to increase photo-thermal signal amplitude. Examples of these efforts can be found in the following published articles: *J. A. Batista et al.*, Anal. Sci. s73 (2001); *G. Tessier et al.*, Appl. Phys. Lett. 78, 2267 (2001); and *G. Tessier et al.*, Rev. Sci. Instrum. 74, 495 (2003). Each of these papers is hereby incorporated herein by reference. The approaches proposed in each of these publications still do not allow for a quantitative comparison of the experimental and theoretical dependencies. For example, in the *Batista et al.* paper, single-wavelength lasers are used to probe the thermal wave field at selected wavelengths, resulting in a set of experimental data that cannot be used for quantitative analysis. In the *Tessier et al.* publications, thermo-reflectance spectra are obtained without use of a pump beam by electrically heating the specimen.

DETAILED DESCRIPTION

Figure 1A:
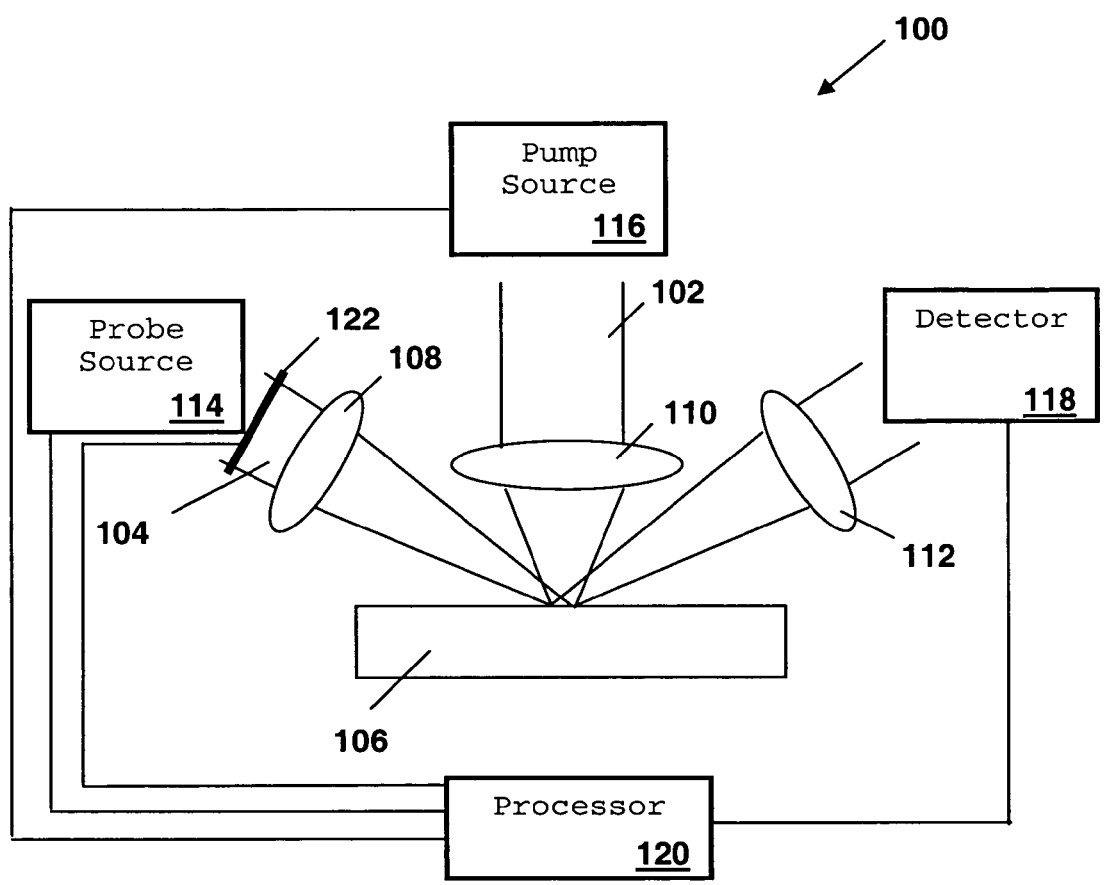
FIG. 1 is a diagram of (a) an oblique angle optical arrangement, (b) a normal angle optical arrangement, and (c) a single beam source arrangement that can be used in accordance with one embodiment of the present invention.

Systems and methods in accordance with embodiments of the present invention can overcome deficiencies in existing modulated optical reflectivity (MOR) systems by taking advantage of the information contained in the spectral dependencies of a thermal wave (TW) response obtained from a sample. Such spectral responses can be compared and/or fitted to corresponding theoretical dependencies in order to obtain more precise and reliable information about the properties of the particular sample.

In accordance with various embodiments of the present invention, a photo-thermal system based on a MOR detection technique can be provided that takes measurements over a range of wavelengths of the probe and/or pump beams. In addition to spectroscopic MOR (SMOR) information, for example, such a system can be used to detect changes in the polarization state of the probe beam, thus providing ellipsometric MOR (EMOR) data.

In one embodiment, a polychromatic probe light source can be used with an intensity-modulated, monochromatic pump beam source, such as a laser light source. The tunable probe light source can include any appropriate light source capable of producing a beam over a wide spectral range, such as a white light source in combination with a monochromater or other wavelength tuner for selecting specific wavelengths in the range, or a broadband light source using a rotatable prism element, diffraction grating, or other dispersive optical element for wavelength selection. Presently, tunable lasers are not able to adjust the output wavelength over a sufficiently large range, such as a range of at least 100 nm, whereby using tunable lasers may not provide the desired wavelength-based information. In other embodiments, a broadband or white light source, such as a tungsten lamp for example, can illuminate the sample with broadband light, and a wavelength selecting device such as a monochromater or prism element can be used to select wavelengths, reflected from the sample, that are passed on to a detector. In yet another embodiment, the broadband light reflected from the sample can be measured by the detector without wavelength selection and/or scanning, such that the detector can measure a number of wavelengths in the range simultaneously (effectively scanning the wavelength range through software or hardware means as known in the art). Such a system can be more complex and/or expensive, however, whereby a system with a tunable light source can be preferable for various applications. The wavelength of the probe beam can be scanned over the wide spectral range, such as a wavelength range of about 300 nm to about 800 nm. In order to obtain useable results from the sample, it can be desirable for the probe beam to scan over a wavelength of at least 100 nm. Using this tunable range, the MOR amplitude can be detected for reflectometry measurements, and the changes in polarization can be detected for ellipsometry measurements. Other parameters can be determined using these and other appropriate measurement methods as would be obvious to one of ordinary skill in the art. Systems for making reflectometry and/or ellipsometry measurements are well known in the art, such that components of systems useful for making these measurements are common and as such will not be described in detail herein. Examples of such systems can be found, however, in the following U.S. Pat. Nos. 5,608,526 and 5,900,939, each of which is hereby incorporated herein by reference.

Figure 1B:
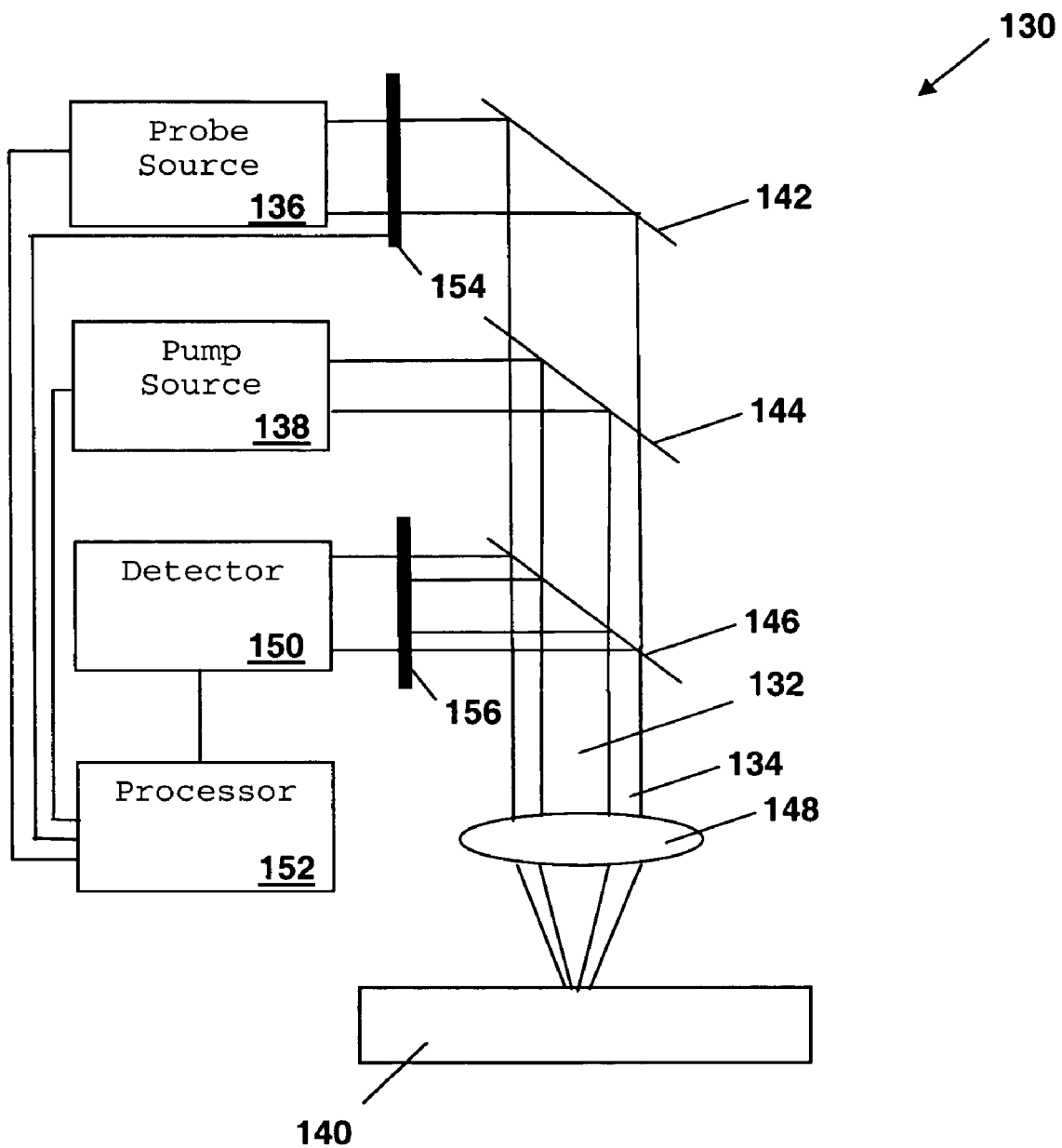
Figure 1C:
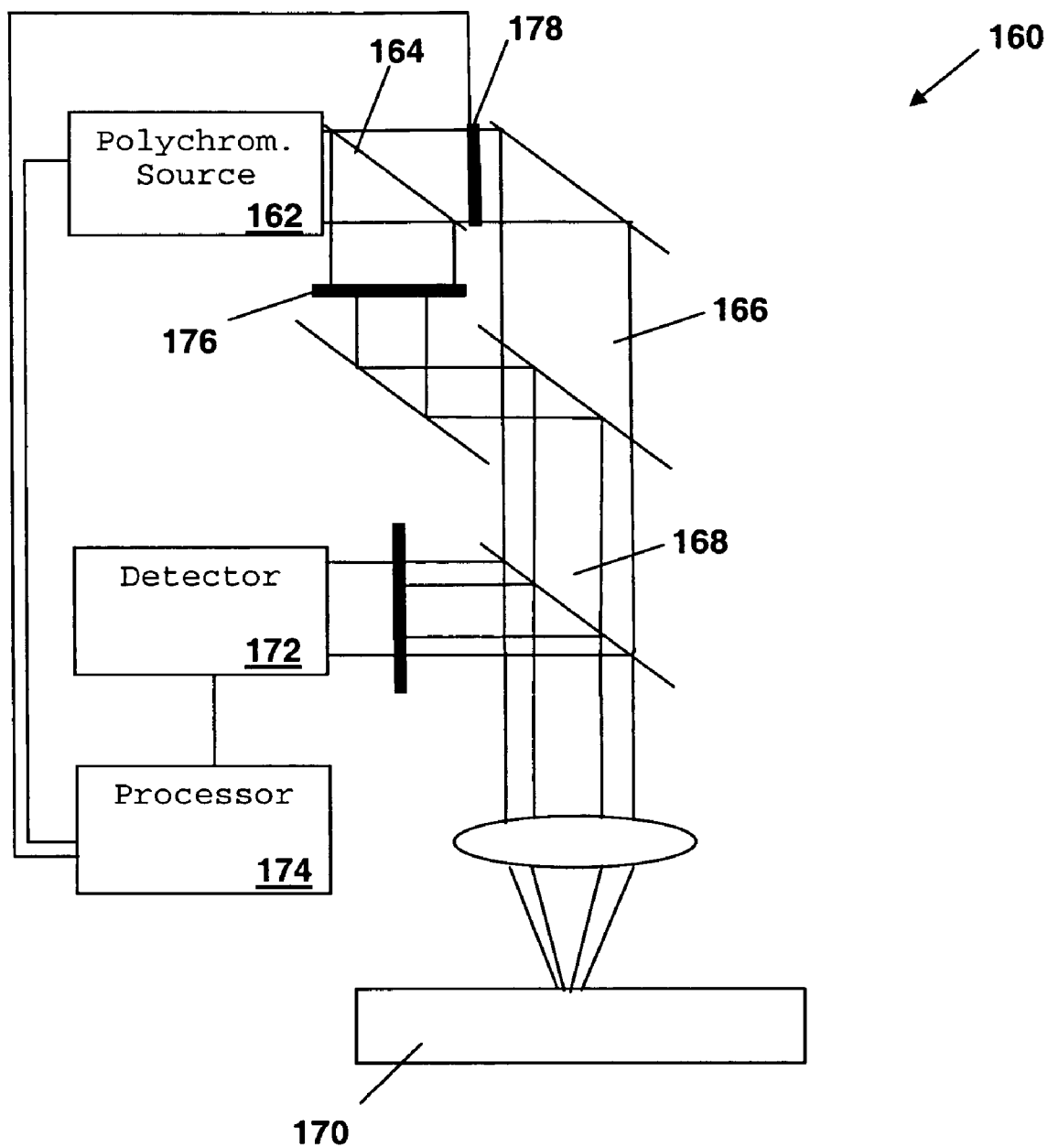

Exemplary optical arrangements that can be used in accordance with embodiments of the present invention are shown in FIGS. 1(a)-1(c). In the arrangement 100 of FIG. 1(a), a monochromatic intensity-modulated pump beam 102 from a pump source 116 such as a laser can be directed so as to be incident upon the sample 106 at a direction that is substantially normal to the (local) plane of the surface of the sample 106 being measured, such as a silicon wafer or semiconductor chip. As discussed above, the pump beam 102 can be used to periodically excite the sample 106, such that thermal and carrier plasma waves are generated that spread out from the pump beam spot inside the sample. These waves can alter the flow of heat and/or carrier plasma from the pump beam spot. A polychromatic probe beam 104 from a probe beam source 114, such as a xenon or other appropriate lamp, can be directed to be incident upon the surface of the sample 106, coincident with the pump beam spot, at an oblique angle. The angle of incidence relative to the plane of the sample can be in the range of about 10° to about 80°. At least a portion of the probe beam 104 then can be reflected from the surface at a similar oblique angle, where the reflected beam portion can be detected by an appropriate detection device 118, such as a photodetector or an array of photodetectors. The detector can generate an output signal that can be provided to a processor 120 for determining characteristics of the sample. The processor 120 also can provide a control signal to the pump and/or probe beam sources, such as to control a scanning of the operating wavelength of at least one of these sources over a wide spectral range. A wavelength tuning device 122, which can include a monochrometer, prism, or other diffractive element, can be used with the pump and/or probe beam to be scanned. The wavelength tuning device can select any of a number of different wavelengths over the desired wavelength range. The wavelength tuning element 122 is shown to be positioned between the probe source 114 and the sample 106, such that a substantially single probe wavelength, or narrow wavelength band, is incident on the sample at a time, where the probe source is broadband. The tuning element 122 also could be placed between the pump source 116 and the sample, where the pump source is broadband, or between the sample and the detector for either a broadband probe or pump beam. For certain embodiments, the wavelength tuning device may be contained within the pump or probe source. The sample 106 can be positioned on an X-Y stage (not shown) that allows the sample 106 to be moved in translation relative to the probe beam 104. Focusing elements 108, 110, 112 can be used to focus the pump and/or probe beams on the sample and/or detector as known in the art.

An alternative arrangement 130 is shown in FIG. 1(b). In this embodiment, both a pump beam 132 from the pump beam source 138 and a probe beam 134 from a probe beam source 136 can be directed at an angle of normal incidence to the (local) plane of the surface of the sample 140, such as by using a reflecting mirror 142 and/or a dichroic mirror 144. Elements 142 and 144 also can be adjustable mirrors, which can be used to adjust a relative position and/or lateral separation of the pump and probe beams on the sample. The pump source 138 can include a modulation frequency variation module as known in the art. A tuning element 154 is shown to be positioned between the probe source 136 and the sample 140, but could alternatively be placed between the pump source 138 and the sample 140 or the sample 140 and the detector 150 as discussed above. A single focusing objective element 138 is shown to be used in this case, in place of the plurality of focusing elements 108, 110, 112 used in the oblique arrangement of FIG. 1(a). The pump and probe beams pass substantially collinearly towards a measurement spot on the sample 140, which can be positioned on a stage such as a rotational stage and/or an X-Y stage (not shown). After striking sample, the reflected pump and probe beams can be redirected by an element such as a beam splitting element 146 (which may require the beams to pass through a polarization rotating element such as a quarter wave plate as known in the art) through a filtering element 150 to remove the pump beam component. The reflected probe beam portion then can be transmitted to a detection apparatus 150, which can generate at least one output signal based on the measured probe beam and provide that output signal to the processor 152. This normal incidence arrangement 130 in general is similar to beam profile reflectometry/ellipsometry configurations such as are used for optical thin film metrology. Examples of such configurations can be found in the following U.S. Pat. Nos. 4,999,014 and 5,042,951.

In another exemplary arrangement 160 shown in FIG. 1(*c*), a single polychromatic source 162 is used that generates a single output beam. The output beam can be split into two beams by a beam splitter 164 or other appropriate optical element. A first of these beams can be passed through an intensity modulator 176 and directed to the surface 170 as a pump beam 168. A second of these beams can be directed to the surface 170 as the probe beam 166. Either of the beams, before or after reflection from the sample, can be wavelength tuned using a wavelength tuning element 178 as discussed with respect to FIGS. 1(*a*) and 1(*b*). The probe beam reflected from the surface can be directed to a detector 172, which can measure properties such as the power of the reflected beam, and provide output signals corresponding to the reflected probe beam to the processor 174 for analysis. In order for only the probe beam to pass to the detector, it can be desirable to filter out the pump beam. Methods for selecting one of a number of collinear beams, such as by controlling a polarization of each beam and then filtering or redirecting a specific polarization, are well known in the art and will not be described in detail herein. The processor 174 can control the wavelength scanning of the single polychromatic source 162 over a wide spectral range, such as by using adjusting a prism or other diffractive element of the wavelength tuning device 154 to select specific wavelengths in that range.

An example of a normal incidence reflectance measurement system is presented in pending U.S. Patent Application Publication No. 2004/0104352, which is hereby incorporated herein by reference. In that example, a modulated reflectance measurement system can make measurements using a probe beam in the near-UV and UV spectrum, and is adaptable for use with fixed or tunable wavelength probe beams. A pump laser and a probe laser are used, each being monochromatic and operating at a different spectrum. The lasers can be diode-based or diode-pumped semiconductor lasers, including solid state laser diodes that have outputs throughout the entire visible spectrum as well as in the infrared and near UV. The lasers are controlled by a processor and a modulator, which causes the pump laser to have an intensity modulated pump beam output. The probe laser produces an output probe beam that is non-modulated (i.e., constant intensity). The probe beam and probe beams are directed through a dichroic mirror to pass collinearly towards a sample positioned on an X-Y stage. After striking sample, the reflected pump and probe beams are redirected by a beam splitter through a filter, which removes the pump beam component, and towards a detector. The detector provides an output signal that is proportional to the power of the reflected probe beam. The output of detector is passed to a filter that includes a lock-in amplifier capable of using the output signal to produce quadrature (Q) and in-phase (I) signals for analysis.

Figure 2:
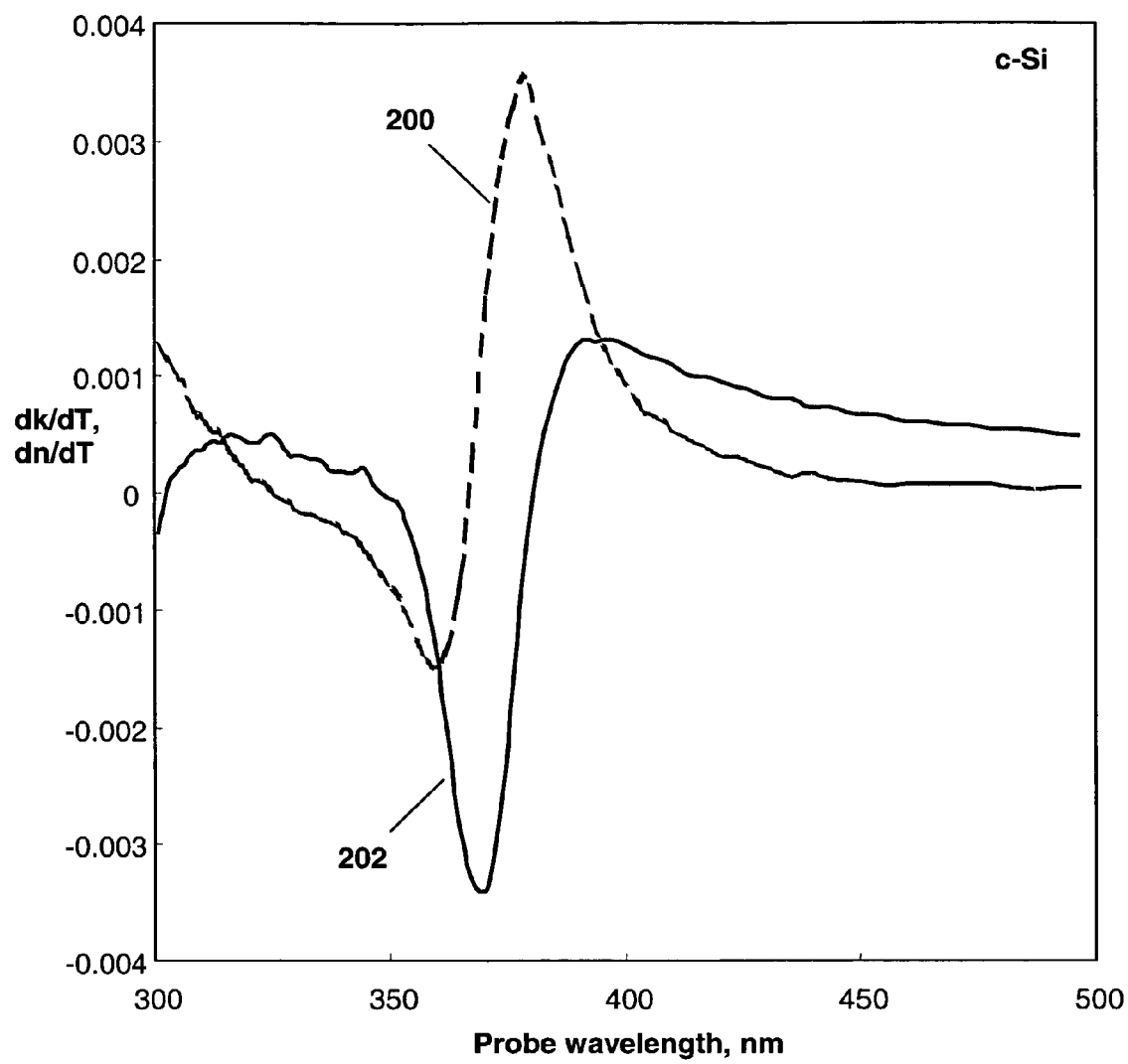
FIG. 2 is a plot showing wavelength dispersion for a c-Si material in accordance with one embodiment of the present invention.

The spectral response of the TW signal can be based on the dispersion of optical constants, such as the refractive index n and the extinction coefficient k, as well as the corresponding temperature coefficients dn/dT and dk/dT. As an example, FIG. 2 shows exemplary wavelength dispersions for a dk/dT measurement 200 and for a dn/dT measurement 202 captured using a crystalline silicon (c-Si) material. Both temperature coefficients change significantly with wavelength, such that the resulting TW signal in this example exhibits large variations as a function of the probe beam wavelength. The probe beam in this example was scanned over a wavelength range from about 300 nm to about 500 nm.

Figure 3:
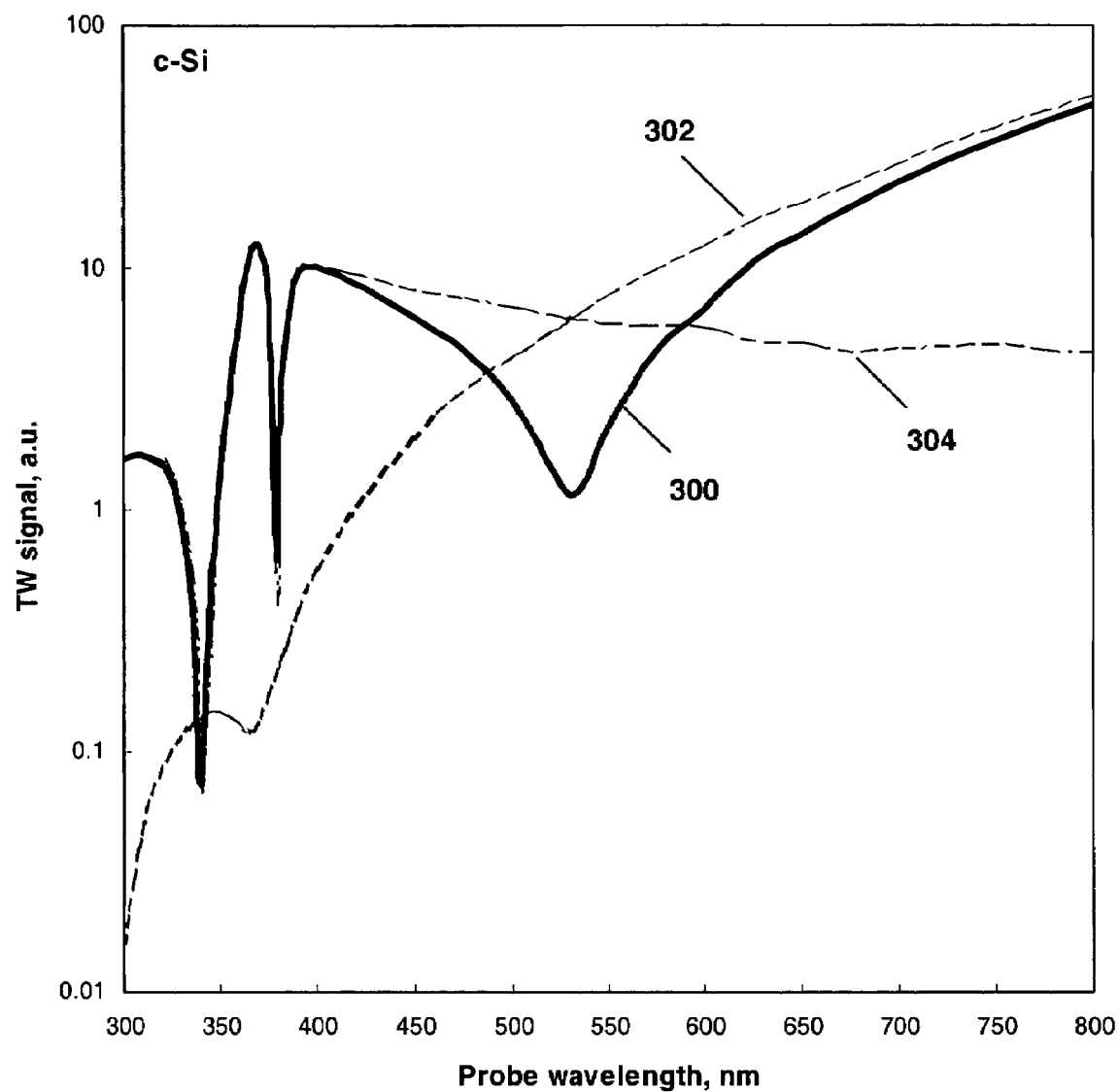
FIG. 3 is a plot showing TW signal as a function of probe beam wavelength in accordance with one embodiment of the present invention.

FIG. 3 shows a TW signal 300 for one c-Si material, calculated as a function of probe beam wavelength. As can be seen, the TW signal 300 varies significantly with probe beam wavelength. A sharp downward peak can be seen in the TW signal near a probe beam wavelength of 550 nm, which is a result of interference between the carrier plasma component 302 of the TW signal and the thermal wave component 304. Near this wavelength, the amplitude of the diminishing carrier plasma component 302 becomes commensurate with that of the rising thermal component 304, leading to the sharp feature seen in TW signal wavelength dependence. At short probe wavelengths, such as those below 400 nm, the TW signal behavior can be seen to be dominated by the thermal component 304. Sharp features observed in the TW signal in this wavelength range are due primarily to c-Si optical dispersion effects coupled with the thermal response of the sample. Features of the TW signal, such as the behavior of the curve and the position of the plasma-thermal transition peak, can be used for comparison and/or fitting to a corresponding theoretical model, as well as for extraction of the thermal, electronic, and optical parameters of a sample, such as a semiconductor chip or silicon wafer.

Figure 4:
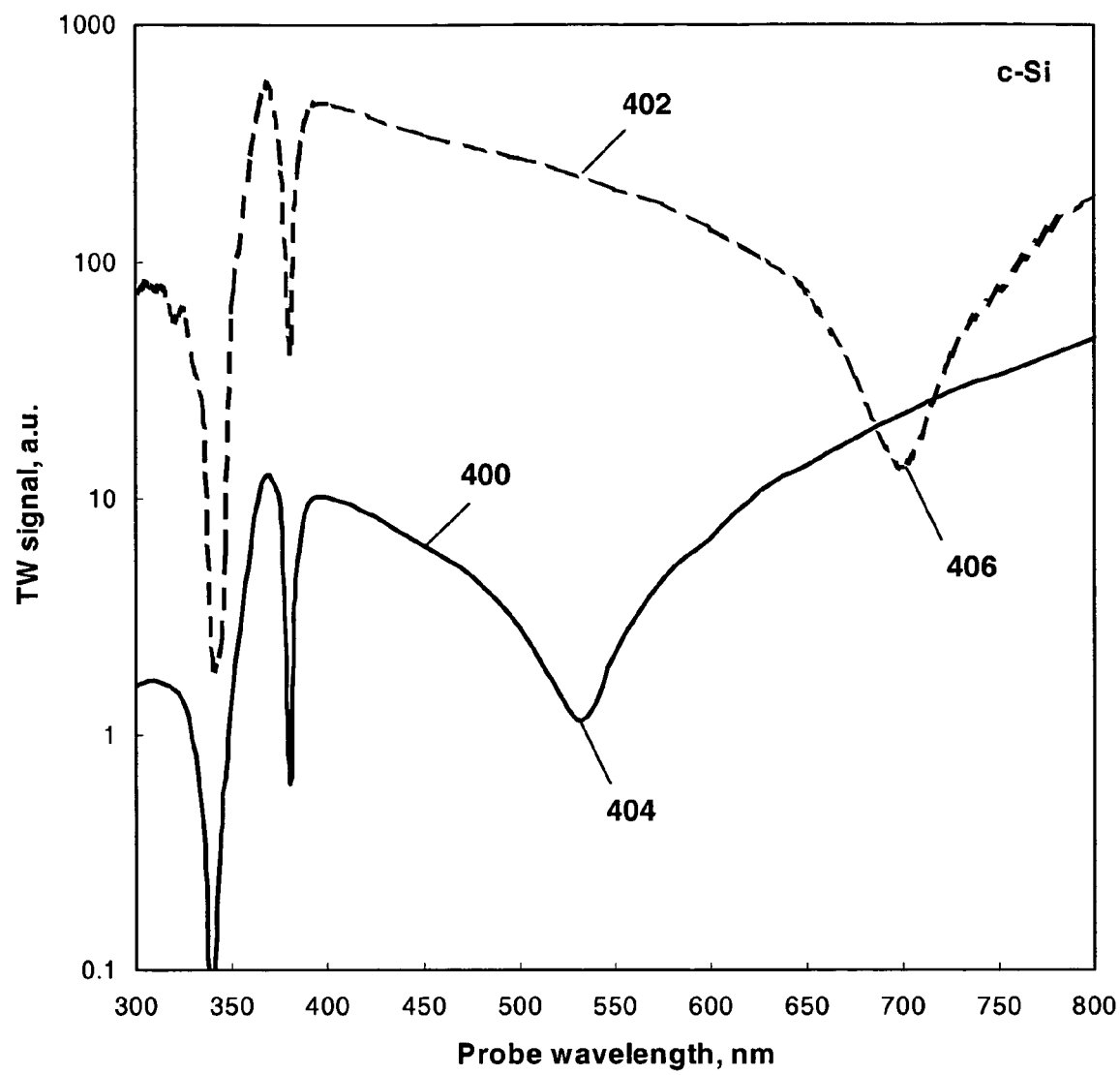
FIG. 4 is a plot showing TW signal as a function of probe beam wavelength for different pump beam wavelengths in accordance with one embodiment of the present invention.

As discussed above with respect to the systems of FIGS. 1(*a*)-1(*c*), a system in accordance with one embodiment of the present invention can utilize a fixed pump beam wavelength, such as a wavelength of about 488 nm from an argon-ion laser, for example. The wavelength of the probe beam then can be scanned, such as over a range between about 300 nm and about 800 nm as in the example of FIG. 4. Curve 400 illustrates changes in the TW signal for a pump wavelength of 780 nm. Significant variation can be seen in the TW curve as a function of probe wavelength. Curve 402 shows a TW signal over the same probe wavelength range, but using a pump beam at 405 nm. It can be seen that varying the pump beam wavelength from 780 nm to 405 nm results in dramatic changes in the TW behavior, particularly in the position of the plasma-to-thermal transition peak 404, 406 in each curve. It therefore can be an advantage to not only scan the probe beam over a large wavelength range, but also to scan the pump beam over a large wavelength range, either alone or in combination with the scanning of the probe beam. For instance, one of the pump and/or probe beams can be scanned over an entire wavelength range for each of a discrete number of wavelengths of the other beam. It can be impractical to attempt to concurrently scan an entire wavelength range of both the pump and probe beams, such that it can be desirable to balance the amount of data to be received with the amount of time per scan. Further, simulations can be run to interpolate between data points for discrete wavelengths where desired. In one approach, each of the pump and probe beams can have data taken at a set of discrete wavelengths, such that a curve fitting routine can be run for the TW signal as a function of both pump beam wavelength and probe beam wavelength over a large wavelength range, such as a range of at least 200 nm.

Figure 5:
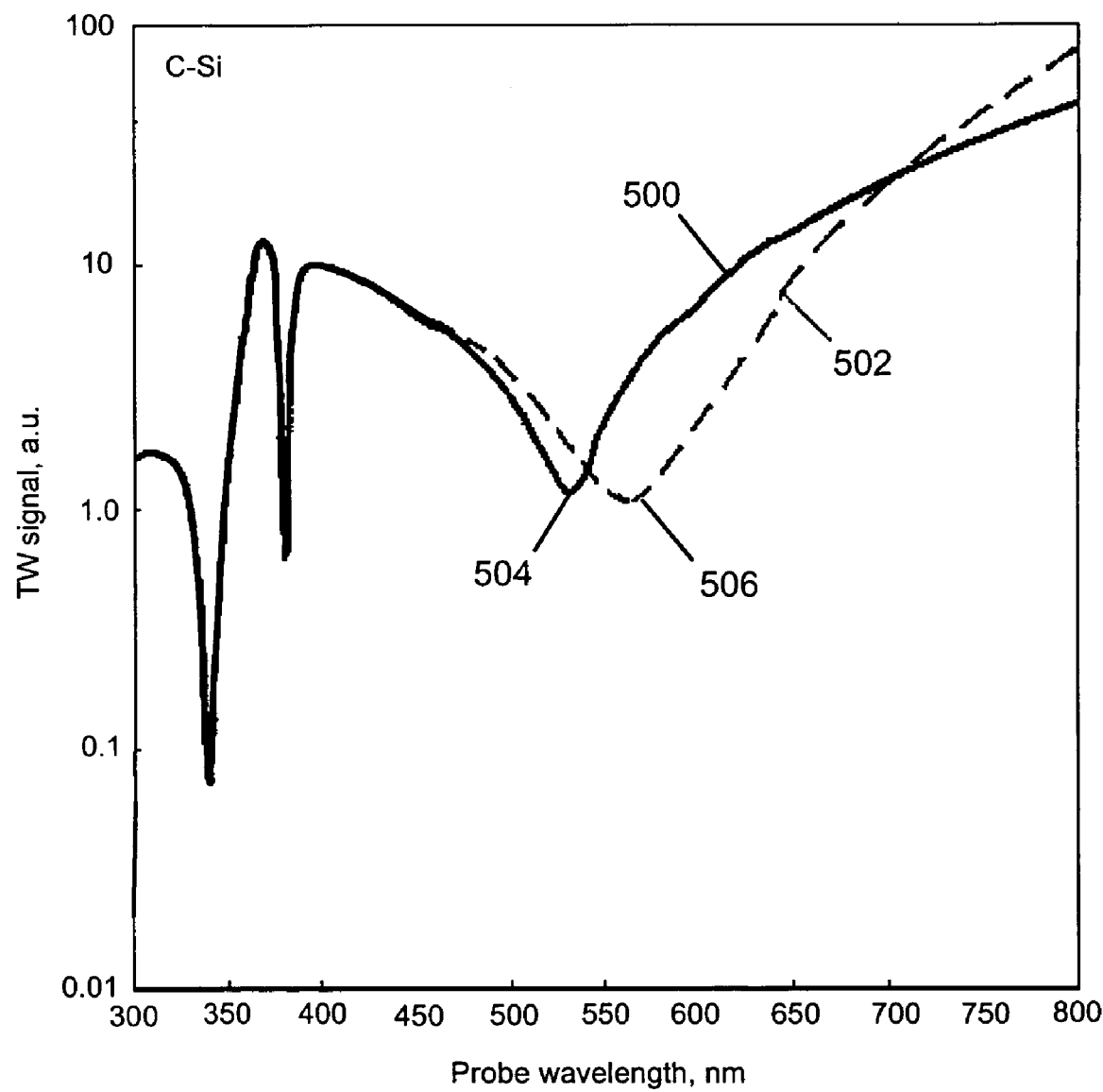
FIG. 5 is a plot showing sensitivity of the spectral TW signal response to variations in electronic parameters of a sample in accordance with one embodiment of the present invention.

The spectral TW response also can vary due to properties of the sample being analyzed, however, such as variations in the electronic parameters of a semiconductor sample. For instance, FIG. 5 shows a curve 500 simulated for a c-Si sample with a first carrier lifetime, and a curve 502 simulated for a c-Si sample with a second carrier lifetime. Again, it can be seen that the plasma-to-thermal peak position 504, 506 changes significantly. Therefore, varying only one of the pump and probe beams may not be sufficient for samples wherein the properties are not well known and/or may vary, either over time or between samples.

Figure 6:
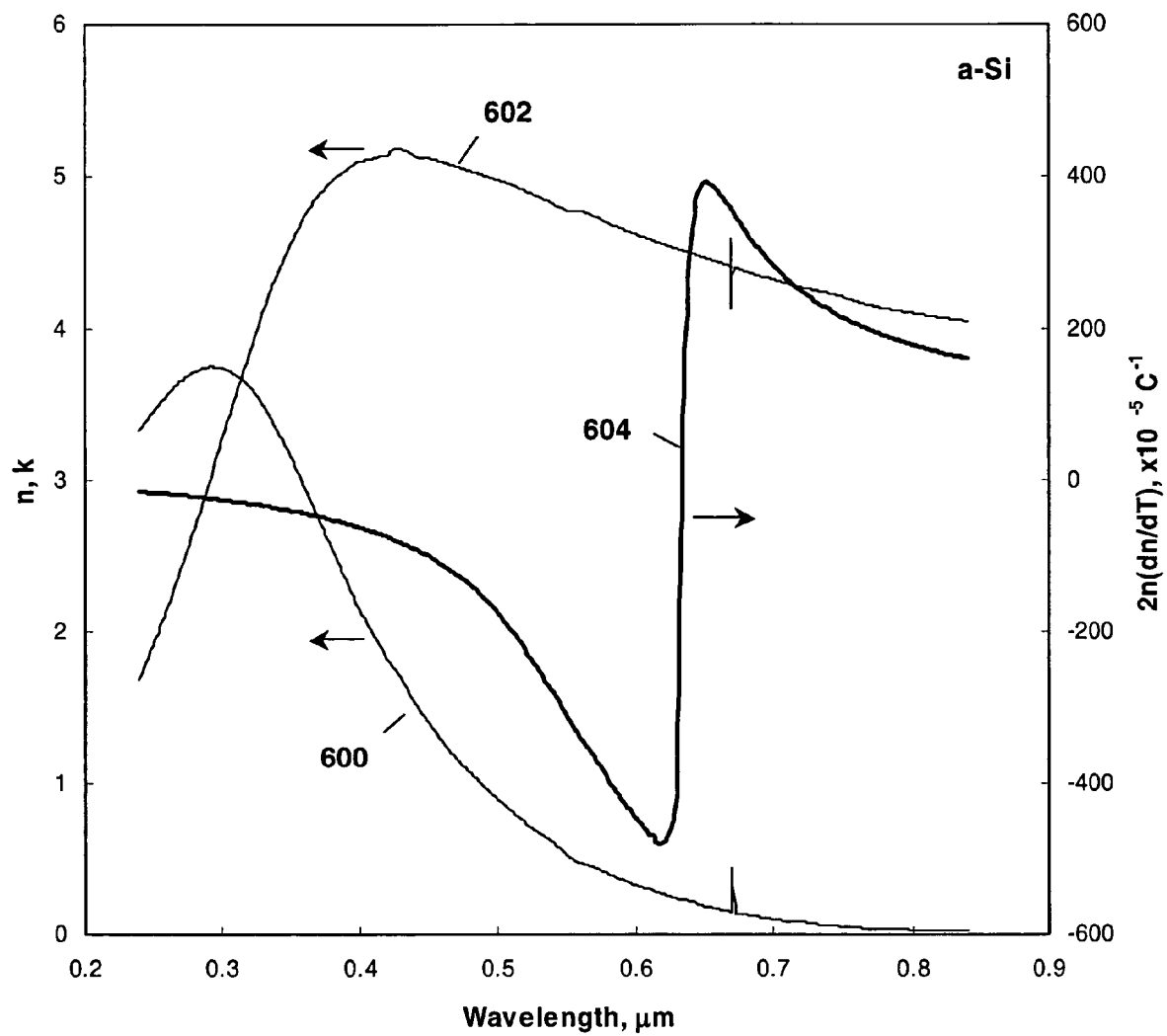
FIG. 6 is a plot showing dispersion characteristics for an a-Si material in accordance with one embodiment of the present invention.
Figure 7:
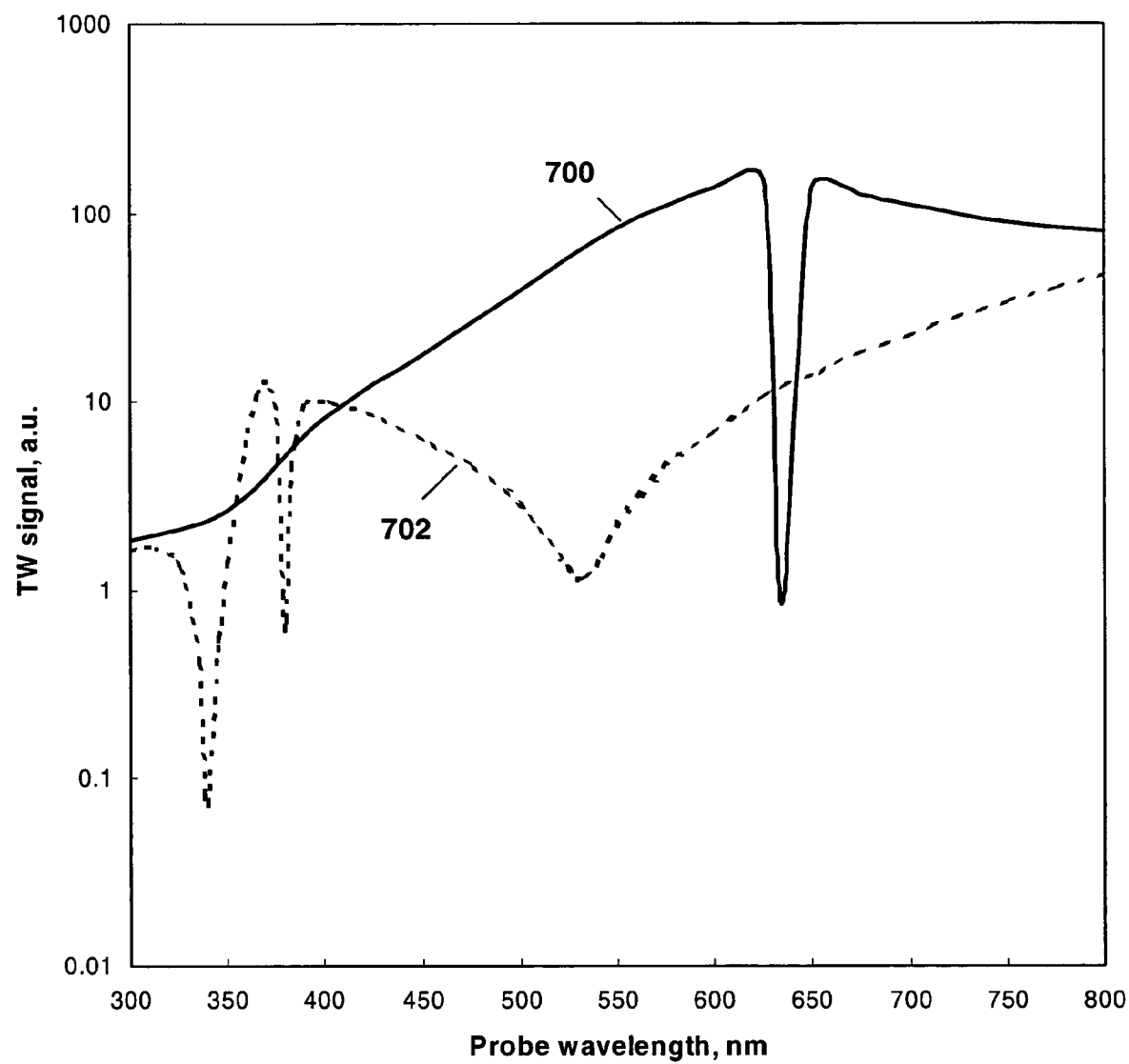
FIG. 7 is a plot showing the TW response for a-Si and c-Si materials in accordance with one embodiment of the present invention.

One primary application of a TW system involves the monitoring of ion implantation and annealing processes. At sufficiently high energies and doses, ion implantation can produce a layer of amorphous silicon (a-Si) material having dispersion characteristics similar to those shown in FIG. 6. In this figure, curve 600 represents the wavelength dependency on refraction index n and curve 602 represents the wavelength dependency on extinction coefficient k. Curve 604 represents the wavelength dependency for 2n(dn/dT). FIG. 7 shows the resulting TW response curve 700 for such an a-Si sample. This curve can be compared to a corresponding TW response for a c-Si material 702, such as is described with respect to FIG. 3. As can be appreciated from this figure, the transition from a damage-free c-Si state to an amorphous state can have a substantial effect on the variation of the TW signal with respect to probe wavelength. This huge difference in TW spectral response, coupled with the corresponding theoretical model, can be used for precise and accurate characterization of ion implant dose. Real samples in ion-implant applications can exhibit behavior between the c-Si and a-Si limiting cases, depending on implantation conditions such as dose and energy.

Figure 8:
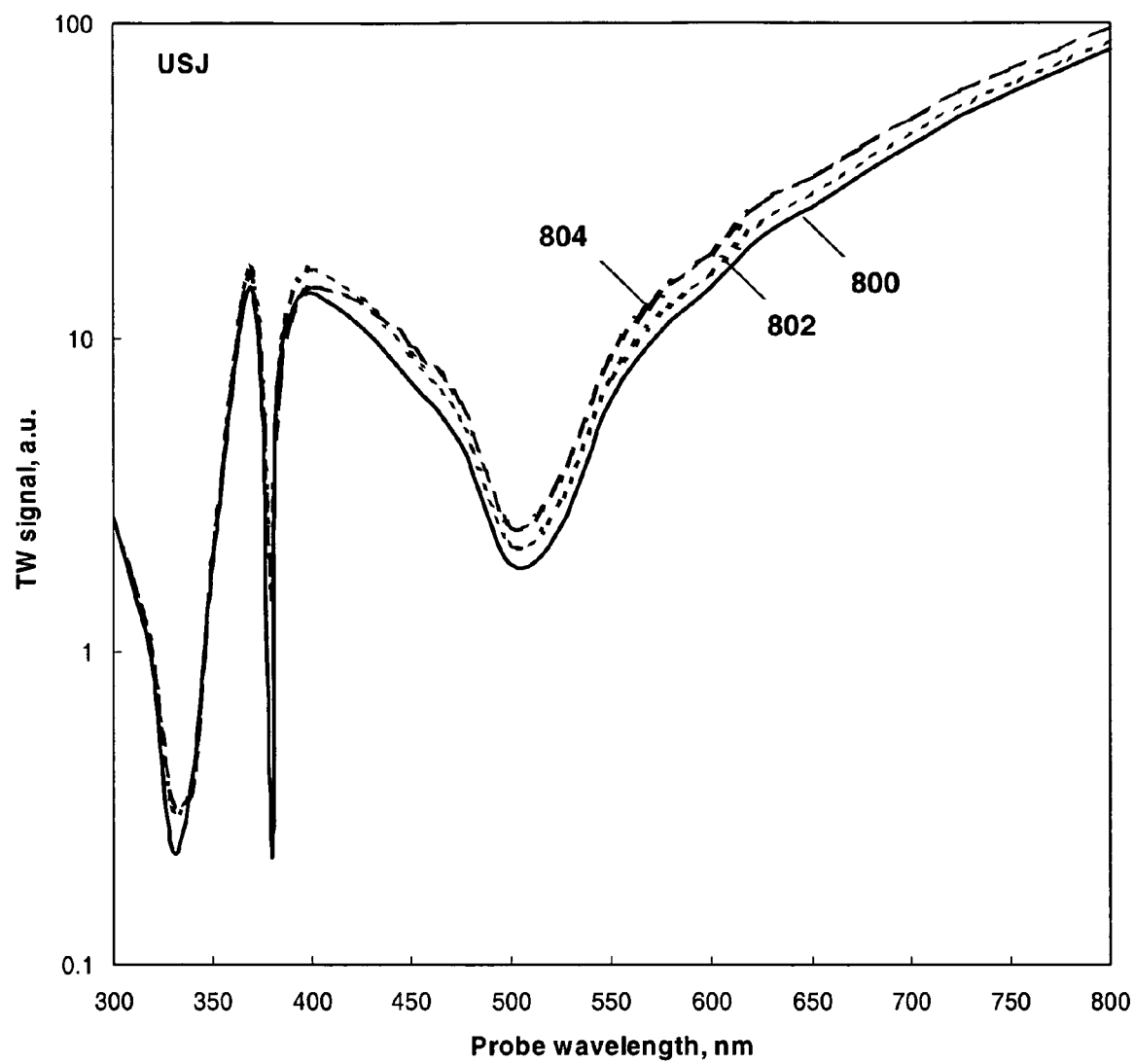
FIG. 8 is a plot showing the TW response for different USJ depths at a first pump beam wavelength in accordance with one embodiment of the present invention.
Figure 9:
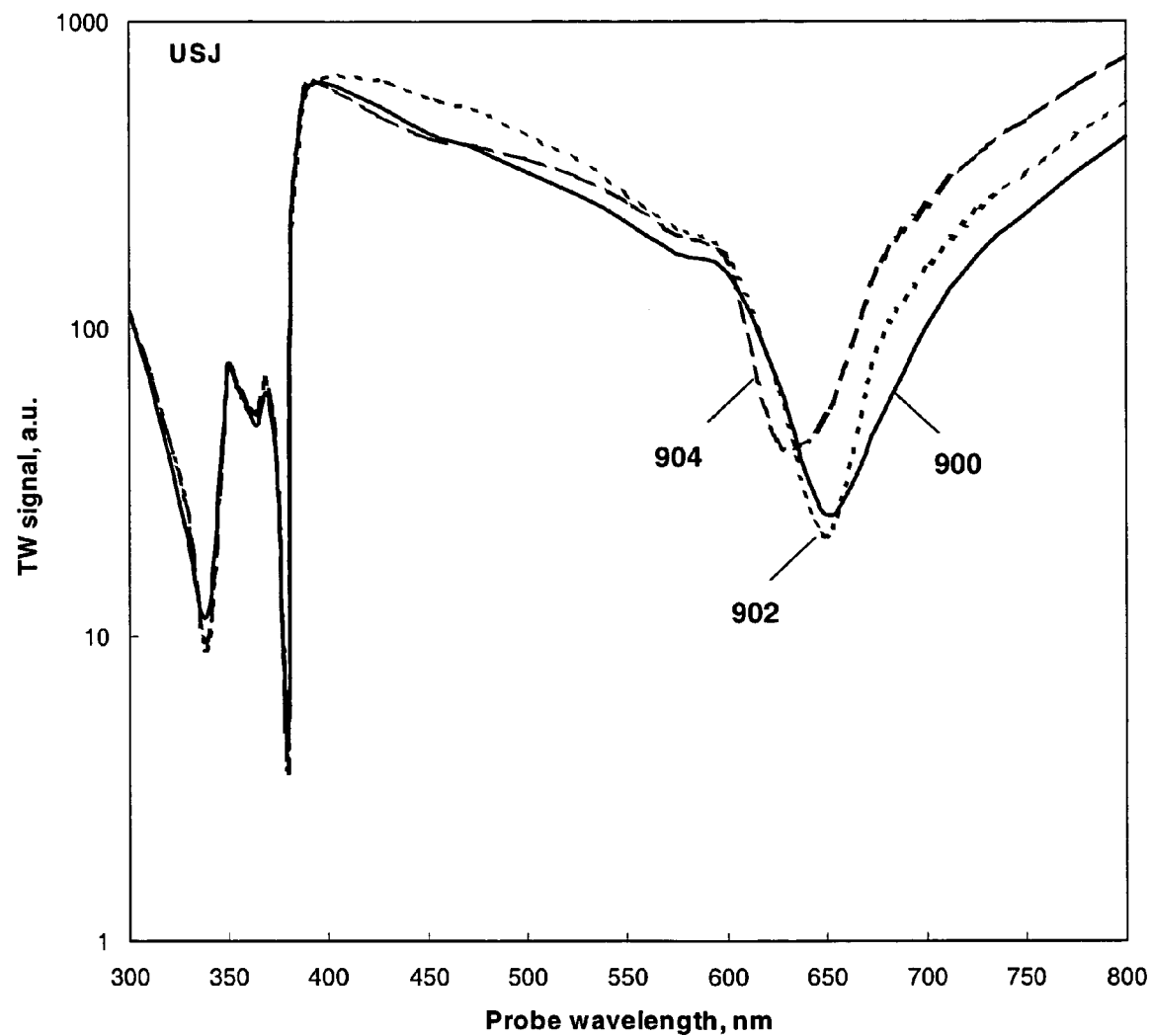
FIG. 9 is a plot showing the TW response for different USJ depths at a second pump beam wavelength in accordance with one embodiment of the present invention.

In the case of ion implanted and annealed samples for ultra-shallow junction (USJ) applications as known in the art, for example, the sensitivity of the system to various USJ parameters, such as junction depth, dopant concentration, and profile shape, can depend strongly on the selection of the pump beam wavelength. FIG. 8 shows the results for TW signal simulations using different USJ depths. For each of these simulations, the pump beam was maintained at a wavelength of about 780 nm. Curve 800 shows the TW signal for a USJ depth of 100 Å, while curve 802 shows the TW signal for a 200 Å depth and curve 804 shows the TW signal for a 300 Å depth. These curves do not show a significant variation in the shape of TW spectral response with respect to variations in USJ thickness. In FIG. 9, however, the wavelength of the pump beam was changed to 405 nm and the simulations were run again. It can be seen that the change in pump beam wavelength results in noticeable variations in plasma-to-thermal peak position for USJ samples with different junction depths. In this example, the USJ depths were 100 Å for curve 900, 300 Å for curve 902, and 500 Å for curve 903. Further, it can be seen that the TW signal behavior at lower probe beam wavelengths, such as in the range between about 300 nm and about 400 nm, demonstrates some variation as well. In this case, it can be beneficial to vary pump beam wavelength instead of, or at least in addition to, scanning the probe beam wavelength.

Various embodiments of the present invention, including at least some of those described above, can be further enhanced by combining these photothermal systems with other techniques and/or systems used and/or being developed in the art. For example, a photothermal system can utilize fiber optics to direct and/or capture light for the pump and/or probe beams. A photothermal system can utilize I-Q data analysis, and/or position modulated MOR detection (PMOR) as known in the art. The photothermal systems described herein also can be combined with any of a number of other techniques, such as photothermal radiometry, four-point probe electrical characterization methodology, and various optical techniques known and/or used in the art.

It should be recognized that a number of variations of the above-identified embodiments will be obvious to one of ordinary skill in the art in view of the foregoing description. Accordingly, the invention is not to be limited by those specific embodiments and methods of the present invention shown and described herein. Rather, the scope of the invention is to be defined by the following claims and their equivalents.

What is claimed is:

1. An apparatus for evaluating the characteristics of a semiconductor sample, comprising:
   an intensity-modulated pump beam, said pump beam being focused to a spot on the surface of the sample for periodically exciting the sample, with the intensity and the modulation frequency of the pump beam being sufficient to create thermal and plasma waves in the sample that modulate the optical reflectivity of the sample;
   a probe beam being directed to a spot on the surface of the sample within a region that has been periodically excited and is reflected therefrom;
   a wavelength scanning device for scanning a wavelength of the probe beam over a spectral range of at least 100 nm in order to vary the relative contribution of the thermal and plasma waves to the modulation of the optical reflectivity of the sample;
   a photodetector for measuring the power of the reflected probe beam at a plurality of wavelengths in the spectral range and generating an output signal in response thereto; and
   a processor operable to receive the output signal and determine a measure of the modulated optical reflectivity of the sample as a function of wavelength.

2. An apparatus according to claim 1, wherein:
   the processor is operable determine a measure of one of the magnitude and phase of the modulated optical reflectivity of the sample as a function of wavelength.

3. An apparatus according to claim 1, further including:
   a filter capable of using the output signal to produce quadrature (Q) and in-phase (I) signals for analysis.

4. An apparatus according to claim 1, wherein:
   said processor is further operable to control the wavelength scanning device in a manner so that a plurality of measurements are taken over the spectral range, with the plurality of measurements being used to evaluate the characteristics of the sample.

5. An apparatus according to claim 1, wherein:
   the spectral range is between about 300 nm and about 800 nm.

6. An apparatus according to claim 1, wherein:
   the wavelength of the probe beam is scanned over a spectral range of at least 200 nm.

7. An apparatus according to claim 1, wherein:
   the wavelength of the probe beam is scanned after being reflected from the sample.

8. An apparatus according to claim 1, wherein:
   the wavelength scanning device includes at least one element selected from the group consisting of monochromaters, prisms, diffraction gratings, and optical diffractive elements.

9. An apparatus according to claim 1, further comprising:
   a steering means for adjusting a lateral separation between the pump and probe beams on the surface of the sample, whereby a plurality of measurements are taken at different lateral separations and the processor uses the measurements at each lateral separation to evaluate the characteristics of the sample.

10. An apparatus according to claim 1, further comprising:
means for varying a modulation frequency of the pump beam, whereby a plurality of measurements are taken at different modulation frequencies to facilitate the evaluation of the sample.

11. An apparatus according to claim 1, wherein:
the photodetector is further capable of measuring an intensity of rays within the reflected probe beam as a function of the angle of incidence with respect to the sample surface at each of the plurality of wavelengths in the spectral range, whereby the processor uses the angle of incidence measurements to evaluate the characteristics of the sample.

12. An apparatus according to claim 1, further comprising:
detector means for measuring a change in polarization state of the reflected probe beam at each of the plurality of wavelengths in the spectral range, whereby the processor uses the polarization state measurements to evaluate the characteristics of the sample.

13. An apparatus according to claim 1, wherein:
the pump beam is monochromatic.

14. An apparatus for evaluating the characteristics of a semiconductor sample, comprising:
an intensity-modulated pump beam, said pump beam being focused to a spot on the surface of the sample for periodically exciting the sample with the intensity and the modulation frequency of the pump beam being sufficient to create thermal and plasma waves in the sample that modulate the optical reflectivity of the sample;
a probe beam being directed to a spot on the surface of the sample within a region that has been periodically excited and is reflected therefrom;
a wavelength scanning device for scanning a wavelength of the pump beam over a spectral range of at least 100 nm in order to vary the relative contribution of the thermal and plasma waves to the modulation of the optical reflectivity of the sample;
a photodetector for measuring the power of the reflected probe beam at each of a plurality of wavelengths of the pump beam in the spectral range, and generating an output signal in response thereto; and
a processor operable to receive the output signal to determine a measure of the modulated optical reflectivity of the sample as a function of the wavelength of the pump beam.

15. An apparatus according to claim 14, wherein:
the processor is operable determine a measure of one of the magnitude and phase of the modulated optical reflectivity of the sample as a function of wavelength.

16. An apparatus according to claim 14, further including:
a filter capable of using the output signal to produce quadrature (Q) and in-phase (I) signals for analysis.

17. An apparatus according to claim 14, wherein:
said processor is further operable to control the wavelength scanning device in a manner so that a plurality of measurements are taken over the spectral range, with the plurality of measurements being used to evaluate the characteristics of the sample.

18. An apparatus according to claim 14, wherein:
the spectral range is between about 300 nm and about 800 nm.

19. An apparatus according to claim 14, wherein:
the wavelength of the pump beam is scanned over a spectral range of at least 200 nm.

20. An apparatus as recited in claim 14, further comprising:
a steering device for adjusting a lateral separation between the pump and probe beams on the surface of the sample, whereby a plurality of measurements are taken at different lateral separations and the processor uses the measurements at each lateral separation to evaluate the characteristics of the sample.

21. An apparatus as recited in claim 14, further comprising:
means for varying a modulation frequency of the pump beam, whereby a plurality of measurements are taken at different modulation frequencies, at each of the plurality of wavelengths, to facilitate the evaluation of the sample.

22. An apparatus as recited in claim 14, wherein:
the photodetector is further capable of measuring an intensity of rays within the reflected probe beam as a function of the angle of incidence with respect to the sample surface at each of the plurality of wavelengths of the pump beam, whereby the processor uses the angle of incidence measurements to evaluate the characteristics of the sample.

23. An apparatus as recited in claim 14, further comprising:
detector means for measuring a change in polarization state of the reflected probe beam at each of the plurality of wavelengths of the pump beam, whereby the processor uses the polarization state measurements to evaluate the characteristics of the sample.

24. An apparatus according to claim 14, wherein:
the pump beam is monochromatic.

25. An apparatus for evaluating the characteristics of a semiconductor sample, comprising:
an intensity-modulated pump beam, said pump beam being focused to a spot on the surface of the sample for periodically exciting the sample, with the intensity and the modulation frequency of the pump beam being sufficient to create thermal and plasma waves in the sample that modulate the optical reflectivity of the sample;
a probe beam being directed to a spot on the surface of the sample within a region that has been periodically excited and is reflected therefrom;
a first wavelength scanning device for scanning a wavelength of a first one of the probe beam and the pump beam over a first spectral range of at least 100 nm in order to vary the relative contribution of the thermal and plasma waves to the modulation of the optical reflectivity of the sample;
a photodetector for measuring the power of the reflected probe beam at a plurality of wavelengths in the spectral range and generating an output signal in response thereto; and
a processor operable to receive the output signal to determine a measure of the modulated optical reflectivity of the sample as a function of wavelength.

26. An apparatus according to claim 25, wherein:
the processor is operable determine a measure of one of the magnitude and phase of the modulated optical reflectivity of the sample as a function of wavelength.

27. An apparatus according to claim 25, further including:
a filter capable of using the output signal to produce quadrature (Q) and in-phase (I) signals for analysis.

28. An apparatus according to claim 25, further comprising:
a second wavelength scanning device for scanning a wavelength of a second one of the probe beam and the pump beam over a second spectral range of at least 100 nm.

29. An apparatus according to claim 28, wherein:
said processor is further operable to control at least one of the first and second wavelength scanning devices in a manner so that a plurality of measurements are taken over the respective first or second spectral range, with the plurality of measurements being used to evaluate the characteristics of the sample.

30. An apparatus according to claim 28, wherein:
at least one of the first and second spectral ranges is between about 300 nm and about 800 nm.

31. An apparatus according to claim 25, further comprising:
a steering device for adjusting a lateral separation between the pump and probe beams on the surface of the sample, whereby a plurality of measurements are taken at different lateral separations and the processor uses the measurements at each lateral separation to evaluate the characteristics of the sample.

32. An apparatus according to claim 25 further comprising:
means for varying a modulation frequency of the pump beam, whereby a plurality of measurements are taken at different modulation frequencies to facilitate the evaluation of the sample.

33. An apparatus according to claim 25, wherein:
the photodetector is further capable of measuring an intensity of rays within the reflected probe beam as a function of the angle of incidence with respect to the sample surface, whereby the processor uses the angle of incidence measurements to evaluate the characteristics of the sample.

34. An apparatus according to claim 25, further comprising:
detector means for measuring a change in polarization state of the reflected probe beam, whereby the processor uses the polarization state measurements to evaluate the characteristics of the sample.

35. An apparatus for evaluating the characteristics of a semiconductor sample, comprising:
a polychromatic beam;
means for splitting the beam into a pump beam and a probe beam, with the pump beam being focused to a spot on the surface of the sample for periodically exciting the sample, with the intensity and the modulation frequency of the pump beam being sufficient to create thermal and plasma waves in the sample that modulate the optical reflectivity of the sample and with the probe beam being directed to a spot on the surface of the sample within a region that has been periodically excited and reflected therefrom;
a wavelength scanning device for scanning a wavelength of at least one of the pump beam, the probe beam, and the polychromatic beam over a spectral range of at least 100 nm in order to vary the relative contribution of the thermal and plasma waves to the modulation of the optical reflectivity of the sample;
a photodetector for measuring the power of the reflected probe beam at a plurality of wavelengths in the spectral range and generating an output signal in response thereto; and
a processor operable to receive the output signal to provide a measure of the modulated optical reflectivity of the sample as a function of wavelength.

36. An apparatus according to claim 35, further comprising:
an intensity modulating device for intensity-modulating the pump beam.

37. An apparatus according to claim 35, further comprising:
means for varying a modulation frequency of the pump beam, whereby a plurality of measurements are taken at different modulation frequencies to facilitate the evaluation of the sample.

38. An apparatus according to claim 35, wherein:
the photodetector is further capable of measuring an intensity of rays within the reflected probe beam as a function of the angle of incidence with respect to the sample surface, whereby the processor uses the angle of incidence measurements to evaluate the characteristics of the sample.

39. An apparatus according to claim 35, further comprising:
detector means for measuring a change in polarization state of the reflected probe beam, whereby the processor uses the polarization state measurements to evaluate the characteristics of the sample.

40. A method for evaluating the characteristics of a semiconductor sample, comprising the steps of:
focusing an intensity-modulated pump beam to a spot on the surface of the sample for periodically exciting the sample, with the intensity and the modulation frequency of the pump beam being sufficient to create thermal and plasma waves in the sample that modulate the optical reflectivity of the sample;
directing a probe beam to a spot on the surface of the sample within a region that has been periodically excited and is reflected therefrom;
scanning a wavelength of the probe beam over a spectral range of at least 100 nm in order to vary the relative contribution of the thermal and plasma waves to the modulation of the optical reflectivity of the sample;
measuring the power of the reflected probe beam at each of a plurality of wavelengths in the spectral range and generating an output signal in response thereto;
filtering the output signals to provide a measure of the modulated optical reflectivity of the sample as a function of wavelength of the probe beam;
using said measurements to calculate one or more parameters of the sample; and
storing the calculated parameters.

41. A method according to claim 40, wherein:
the spectral range is between about 300 nm and about 800 nm.

42. A method according to claim 40, wherein:
the wavelength of the probe beam is scanned over a spectral range of at least 200 nm.

43. A method according to claim 40, further comprising:
adjusting a lateral separation between the pump and probe beams on the surface of the sample, whereby a plurality of measurements are taken at different lateral separations and the measurements at each lateral separation are used to evaluate the characteristics of the sample.

44. A method according to claim 40, further comprising:
varying a modulation frequency of the pump beam, whereby a plurality of measurements are taken at different modulation frequencies to facilitate the evaluation of the sample.

45. A method according to claim 40, further comprising:
measuring an intensity of rays within the reflected probe beam as a function of the angle of incidence with respect to the sample surface at each of the plurality of wavelengths in the spectral range, whereby the angle of incidence measurements are used to evaluate the characteristics of the sample.

46. A method according to claim 40, further comprising:
measuring a change in polarization state of the reflected probe beam at each of the plurality of wavelengths in the spectral range, whereby the processor uses the polarization state measurements to evaluate the characteristics of the sample.

47. A method according to claim 40, wherein:
the pump beam is monochromatic.

48. A method for evaluating the characteristics of a semiconductor sample, comprising the steps of:
focusing an intensity-modulated pump beam to a spot on the surface of the sample for periodically exciting the sample, with the intensity and the modulation frequency of the pump beam being sufficient to create thermal and plasma waves in the sample that modulate the optical reflectivity of the sample;
directing a probe beam to a spot on the surface of the sample within a region that has been periodically excited and is reflected therefrom;
scanning a wavelength of the pump beam over a spectral range of at least 100 nm in order to vary the relative contribution of the thermal and plasma waves to the modulation of the optical reflectivity of the sample;
measuring the power of the reflected probe beam at each of a plurality of wavelengths in the spectral range and generating an output signal in response thereto;
filtering the output signals to provide a measure of the modulated optical reflectivity of the sample as a function of wavelength of the pump beam;
using said measurements to calculate one or more characteristics of the sample and
storing the calculated characteristics.

49. A method according to claim 48, wherein:
the spectral range is between about 300 nm and about 800 nm.

50. A method according to claim 48, wherein:
the wavelength of the probe beam is scanned over a spectral range of at least 200 nm.

51. A method according to claim 48, further comprising:
adjusting a lateral separation between the pump and probe beams on the surface of the sample, whereby a plurality of measurements are taken at different lateral separations and the measurements at each lateral separation are used to evaluate the characteristics of the sample.

52. A method according to claim 48, further comprising:
varying a modulation frequency of the pump beam, whereby a plurality of measurements are taken at different modulation frequencies to facilitate the evaluation of the sample.

53. A method according to claim 48, further comprising:
measuring an intensity of rays within the reflected probe beam as a function of the angle of incidence with respect to the sample surface at each of the plurality of wavelengths in the spectral range, whereby the angle of incidence measurements are used to evaluate the characteristics of the sample.

54. A method according to claim 48, further comprising:
measuring a change in polarization state of the reflected probe beam at each of the plurality of wavelengths in the spectral range, whereby the processor uses the polarization state measurements to evaluate the characteristics of the sample.

55. A method according to claim 48, wherein:
the probe beam is monochromatic.

56. A method for evaluating the characteristics of a semiconductor sample, comprising the steps of:
focusing an intensity-modulated pump beam to a spot on the surface of the sample for periodically exciting the sample, with the intensity and the modulation frequency of the pump beam being sufficient to create thermal and plasma waves in the sample that modulate the optical reflectivity of the sample;
directing a probe beam to a spot on the surface of the sample within a region that has been periodically excited and is reflected therefrom;
scanning a wavelength of at least one of the pump beam and probe beam over a spectral range of at least 100 nm in order to vary the relative contribution of the thermal and plasma waves to the modulation of the optical reflectivity of the sample;
measuring the power of the reflected probe beam at each of a plurality of wavelengths in the spectral range and generating an output signal in response thereto;
filtering the output signals to provide a measure of the modulated optical reflectivity of the sample as a function of wavelength of the pump and probe beams;
using said measurements to calculate one or more characteristics of the sample; and
storing the calculated characteristics.

57. A method for evaluating the characteristics of a semiconductor sample, comprising the steps of:
splitting a polychromatic beam into a pump beam and a probe beam;
modulating an intensity of the pump beam;
focusing the intensity-modulated pump beam to a spot on the surface of the sample for periodically exciting the sample, with the intensity and the modulation frequency of the pump beam being sufficient to create thermal and plasma waves in the sample that modulate the optical reflectivity of the sample;
directing the probe beam to a spot on the surface of the sample within a region that has been periodically excited and is reflected therefrom;
scanning a wavelength of at least one of the pump beam, the probe beam, and the polychromatic beam over a spectral range of at least 100 nm in order to vary the relative contribution of the thermal and plasma waves to the modulation of the optical reflectivity of the sample;
measuring the power of the reflected probe beam at each of a plurality of wavelengths in the spectral range and generating an output signal in response thereto;
filtering the output signals to provide a measure of the modulated optical reflectivity of the sample as a function of wavelength of the pump beam;
using said measurements to calculate one or more characteristics of the sample; and
storing the calculated characteristics.

58. An apparatus for evaluating the characteristics of a semiconductor sample, comprising:

an intensity-modulated pump beam, said pump beam being focused to a spot on the surface of the sample for periodically exciting the sample, with the intensity and the modulation frequency of the pump beam being sufficient to create thermal and plasma waves in the sample that modulate the optical reflectivity of the sample;

a broadband light source for generating a probe beam;

a wavelength tuner for tuning a wavelength of the probe beam over a spectral range of at least 100 nm in order to vary the relative contribution of the thermal and plasma waves to the modulation of the optical reflectivity of the sample;

optics to direct the tuned wavelength probe beam to a spot on the surface of the sample within a region that has been periodically excited and is reflected therefrom; and a photodetector for measuring the power of the reflected probe beam at a plurality of wavelengths in the spectral range; and a processor operable to receive an output signal from the photodetector and determine a measure of the modulated optical reflectivity of the sample as a function of wavelength.

59. An apparatus according to claim 58, wherein:

the processor is operable determine a measure of one of the magnitude and phase of the modulated optical reflectivity of the sample as a function of wavelength.

60. An apparatus according to claim 58, further including:

a filter capable of using the output signal to produce quadrature (Q) and in-phase (I) signals for analysis.

* * * * *